United States Patent
Castellarnau

(10) Patent No.: US 8,702,979 B2
(45) Date of Patent: Apr. 22, 2014

(54) METHOD FOR DETERMINING THE REDUCTION RATIO OR THE KT/V VALUE OF A KIDNEY SUBSTITUTION TREATMENT AND APPARATUS FOR THE REALISATION OF THE METHOD

(75) Inventor: Alex Castellarnau, Suzhou (CN)

(73) Assignee: B. Braun Avitum AG, Melsungen (DE)

( * ) Notice: Subject to any disclaimer, the term of this patent is extended or adjusted under 35 U.S.C. 154(b) by 908 days.

(21) Appl. No.: 12/665,150

(22) PCT Filed: Jun. 20, 2008

(86) PCT No.: PCT/IB2008/001616
§ 371 (c)(1),
(2), (4) Date: Apr. 21, 2010

(87) PCT Pub. No.: WO2009/013575
PCT Pub. Date: Jan. 29, 2009

(65) Prior Publication Data
US 2010/0213127 A1 Aug. 26, 2010

(30) Foreign Application Priority Data
Jun. 20, 2007 (EP) .................................. 07012040

(51) Int. Cl.
*B01D 35/00* (2006.01)
*B01D 35/14* (2006.01)

(52) U.S. Cl.
USPC .............................. 210/88; 210/87; 210/647

(58) Field of Classification Search
USPC .................................................. 210/88, 647
See application file for complete search history.

(56) References Cited

U.S. PATENT DOCUMENTS

| 5,685,988 A | 11/1997 | Malchesky |
| 6,258,027 B1 * | 7/2001 | Sternby ......................... 600/366 |
| 6,666,840 B1 * | 12/2003 | Falkvall et al. .............. 604/5.04 |

FOREIGN PATENT DOCUMENTS

| WO | WO 94/08641 | 4/1994 |
| WO | WO 98/19592 | 5/1998 |
| WO | WO 98/55166 | 12/1998 |
| WO | WO 99/62574 | 12/1999 |

OTHER PUBLICATIONS

Written Opinion dated Nov. 21, 2008; Appl. No. PCT/IB2008/001616.
International Search Report dated Nov. 21, 2008; Appl. No. PCT/IB2008/001616.

* cited by examiner

*Primary Examiner* — Dirk Bass
(74) *Attorney, Agent, or Firm* — RatnerPrestia

(57) ABSTRACT

A method for determining online adequacy parameters for any hemodialysis, hemofiltration and hemodiafiltration treatment modality is provided. Blood equilibrated dialysate samples at the begin and/or at the end of the treatment; and a continuous measurements of waste compounds in the effluent dialysate by means of spectroscopic techniques, are required. With the data coming from the measurements and a simple mathematic approach Kt/V and reduction ratios for different compounds, which are important from the medical point of view, are obtained.

7 Claims, 4 Drawing Sheets

METHOD FOR DETERMINING THE REDUCTION RATIO OR THE KT/V VALUE OF A KIDNEY SUBSTITUTION TREATMENT AND APPARATUS FOR THE REALISATION OF THE METHOD

This is a U.S. National Phase application of application number PCT/IB2008/001616, filed Jun. 20, 2008 (which is incorporated herein by reference in its entirety), which claims priority benefit of EP 07012040.7 (filed Jul. 20, 2007).

The present invent relates generally to kidney substitution treatment and more particularly is directed to a method and an apparatus for on line real time monitoring the adequacy and the effectiveness of the kidney substitution treatment. Even more particular the invention relates to a method and an apparatus for determining the reduction ratio or the Kt/V value of a kidney substitution treatment.

Patients who have reduced kidney functions or no kidney function at all have to get rid of waste products, including toxic substances, by kidney substitution treatments. During such a kidney substitution treatment the patient is connected to an extracorporeal blood circuit. In that extracorporeal blood circuit the blood of the patient is contacted with a kidney substitution treatment liquid via the kidney substitution which is in general a membrane. The kidney substitution treatment liquid containing different salts in such a concentration that the waste products in the blood by diffusion and convection pass through the membrane into the kidney substitution treatment liquid. The kidney substitution treatment liquid is flowing from a reservoir via the kidney substitution to a drain.

During the kidney substitution treatment the adequacy and the effectiveness, respectively, of the treatment is very important. In other words, it is necessary to be able to control the adequacy and the effectiveness, respectively, of the kidney substitution treatment on line, i.e. while the treatment is in progress. In order to secure an adequate and effective kidney substitution treatment the Kt/V (urea) model has been developed, where K [ml/min] is the effective clearance for urea, t [min] is the treatment time and V [ml] is the urea distribution volume which matches the total body water. Furthermore the reduction ratio (RR) of a waste product out of the blood is another method to estimate the adequacy and the effectiveness, respectively, of the kidney substitution treatment The NCDS (National Cooperative Dialysis Study) and the HEMO (Hemodialysis) study found, after analyzing a large patient group, that morbidity and mortality in end stage renal disease (ESRD) was strongly correlated with the Kt/V value or dialysis dose. Data obtained from these studies resulted in guidelines regarding hemodialysis treatments, which demand a minimum dose of Kt/V=1.2 generally and 1.4 for diabetics respectively (Dialysis Outcomes Quality Initiative guidelines). It is worthy to point out that a morbidity decrease not only improves the patient well-being, but also reduces significantly the medical costs as the patient requires less care. The need of a reliable and cost effective method to monitor the Kt/V or the RR and by extension control kidney substitution treatment adequacy and morbidity, is therefore easily understood.

In the Kt/V calculation, the main problems are K and V estimation along with the multi-compartment urea kinetics. V can be estimated by bioimpedance, anthropometric measurements or applying the urea kinetic model (UKM). All these methods have a certain degree of error. K can be estimated so far by measuring the urea blood concentration before and after the treatment or by monitoring conductivity changes of the kidney substitution liquid on the inlet and outlet of the kidney substitution device.

Blood samples method is the reference one. After taking the blood samples and applying either UKM or Daugirdas formula (Daugirdas JT. The post:pre-dialysis plasma urea nitrogen ratio to estimate Kt/V and nPCR: mathematical modeling. Int J Artif Organs. 1989:12:411-19) a single pool Kt/V (spKt/V) is estimated. Furthermore Daugirdas second generation formulas (Daugirdas J T. Second generation logarithmic estimates of single-pool variable volume Kt/V: an analysis of error. J Am Soc Nephrol. 1993;4:1205-13) should be used to get an equilibrated Kt/V (eKt/V) which accounts for the urea rebound caused by the fact that urea kinetics does not follow a single pool model but a multi-compartment one. This method has two main problems: it is not possible to know whether the treatment is adequate or not before it finished. Therefore it is not possible to perform any action to improve the situation; insofar it is not an easy to apply method: sampling time is very important to get an accurate value, and the medical staff must send the samples to the lab, wait for the results and calculate Kt/V values with the help of a computer. These facts result on a monthly basis Kt/V measurements in the best cases, which means that in worst case scenario a patient might be under-dialyzed for one whole month.

Conductivity methods are based on the discovery that sodium clearance is almost equal to urea clearance and that the relationship between conductivity and the sodium concentration of the kidney substitution treatment liquid can be considered linear on the temperature range of interest. Therefore it is possible to get urea clearance by measuring the sodium diffusion transport through the membrane in the kidney substitution device.

It is important to introduce the concept of Dialysance as it slightly differs from Clearance. Clearance is defined as the ratio between transport rate and concentration multiplied by flow, and it is applicable when the diffusing substance is on the blood side but not on the side of the kidney substitution treatment liquid. Dialysance is defined as the ratio between transport rate and concentration gradient multiplied by flow, and it is applicable when the diffusing substance is on both sides of the membrane of the kidney substitution device. When one applies conductivity methods to measure urea Clearance, one actually measures sodium Dialysance (Depner T., Garred L. Solute transport mechanisms in dialysis. Hörl W., Koch K., Lindsay R., Ronco C., Winchester J F., editors. Replacement of renal function by dialysis, 5$^{th}$ ed. Kluwer academic publishers, 2004:73-91).

During conductivity based clearance measurements, a kidney substitution treatment liquid inlet conductivity different to the blood one is produced, which results in a net transfer of sodium either from blood to kidney substitution treatment liquid or from kidney substitution treatment liquid to blood due to the generated gradient. There are currently three patented methods which are applied in the industry: step conductivity profile, step conductivity profile and integration of conductivity peaks (Polaschegg H D, Levin N W. Hemodialysis machines and monitoris. Hörl W, Koch K, Lindsay R, Ronco C, Winchester J F, editors. Replacement of renal function by dialysis, 5$^{th}$ ed. Kluwer academic publishers, 2004: 414-418).

The main advantages of such approaches are: they are relatively easy to implement and cost effective as they only need an extra conductivity/temperature sensor downstream the dialyzer; they offer Kt/V measurements during the treatment allowing the medical staff to react and perform some actions in case the treatment is not going as it should.

However, conductivity based methods have also some limitations:

they can induce some sodium load in the patient during the measurement;

they are not useful to obtain other interesting parameters like nPCR (normalized Protein Catabolic Rate) or TRU (Total Removed Urea);

the maximum measurement frequency offered so far by the industry is about 20 minutes; that means that in a worst case scenario the patient could be under-dialyzed for 20 minutes; and, although there are some publications and patents regarding it, so far, conductivity methods have not been applied with enough reliability to kidney substitution treatments.

Another method to estimate the adequacy of kidney substitution treatments is by direct measurement of the waste products (i.e. urea) concentration in the effluent kidney substitution treatment liquid. With such approach two options are available and both avoid the need of K or V estimation as expressed above.

One option assumes that the evolution of urea concentration over the time in the side of the effluent kidney substitution treatment liquid is proportional to the one in the blood. Therefore the slope of the line obtained after applying the natural logarithm to the registered concentration values over the time will be the same on both sides: effluent kidney substitution treatment liquid and blood, and by definition such slope is K/V. The problem of this approach can be described as "What is in the blood is not in the effluent kidney substitution treatment liquid". If one has a clearance impairment during the treatment, less urea diffuses to the side of the kidney substitution treatment liquid resulting on a higher slope and a higher Kt/V, which suggests a better dialysis when in fact it is worse as you can see in FIG. 5.

The second option is described in EP 0986410 and consists on the so called "Whole body clearance" wbKt/V. Sternby has found a good correlation between wbKt/V and Daugirdas eKt/V (Sternby J. Whole body Kt/V from dialysate urea measurements during hemodialysis. J Am Soc Nephrol. 1998 Nov;9(11):2118-23.). This approach considers that in a normal treatment K can be assumed constant during some time intervals, and uses such data to calculate backwards the adequacy parameters. Even though it is more secure than the previous approach it still relies on the assumption of constant conditions during such time intervals, and it cannot offer wbKt/V values from the beginning of the treatment.

The methods available so far to measure online the concentration of waste products in effluent kidney substitution treatment liquid are urea sensors and UV spectrophotometry. The limitations of the urea sensors are well known. Recent works carried out by Fridolin et al (Uhlin F. Haemodialysis treatment monitored online by ultra violet absorbance. Linkoping University Medical Dissertations n° 962. Department of Medicine and Care Division of Nursing Science & Department of Biomedical Engineering. 2006.) have shown UV spectrophotometry as a reliable and cost affordable method to monitor waste products in effluent kidney substitution treatment liquid. Such an apparatus has been already described in EP 1083948.

It has been shown that a very good correlation exists between the UV absorbance of the effluent kidney substitution treatment liquid and the concentrations of the waste products, ie. urea, creatinine, uric acid, phosphates, β2-microglobulin and other compounds, in the effluent kidney substitution treatment liquid. Since it is possible to know the concentration of the waste products urea which are removed during every treatment, it is not only possible to calculate Kt/V by means of natural logarithm slope as described above, but also obtain other important parameters like TRU and nPCR. Besides, a graph of the absorbance evolution over the time can be presented on a display of a kidney substitution device, it will give reliable and online feedback information to the medical staff just a few seconds after any performed action. This method, however, has so far two major shortcomings: it is not able to detect a clearance impairment, on the contrary it will offer a better Kt/V in such a case as described above and the good correlation between absorbance and the different waste products in the effluent kidney substitution treatment liquid falls dramatically when data from different patients are analyzed together. It requires therefore a regression line in an individual basis, which is impracticable from the clinical point of view.

Subject of the present invention is to provide a method to overcome the problems described above and determining online adequacy parameters for any kidney substitution treatment. Another goal of the invention is to provide an apparatus for the realisation of the method.

With the present invention is it possible to provide a method and an apparatus to obtain online Kt/V or RR without the needs of a patient based regression line, provide a method and an apparatus to obtain online Kt/V or RR without the need of getting the slope value after applying the natural logarithm to the concentration over the time profile, and therefore avoid the inherent overestimation risks, provide a method and an apparatus not only to obtain online Kt/V, but also online RR (Reduction Ratio), provide a method and an apparatus, fulfilling the previous requirements, able to get adequacy parameters for any available kidney substitution treatment, i.e. single and double needle hemodialysis, pre-dilution, post-dilution and pre-post-dilution hemofiltration, provide a method and an apparatus, fulfilling the previous requirements, to not only measure urea clearance but clearances of other important compounds from the clinical point of view like b2-microglobulin, phosphates, creatinine or uric acid, Our invention requires an equilibrated sample of kidney substitution treatment liquid at the beginning of the treatment as described in patent WO 94/08641, however the method described in that patent consists in stationary kidney substitution treatment liquid within the kidney substitution which equilibrates with blood, being the time to equilibration an arbitrary value of around 5 minutes which can be guessed empirically considering the blood flow and the used kidney substitution. The present invention propose a new approach consisting in a recirculation of the kidney substitution treatment liquid with the blood, during this stage we can monitor the equilibration procedure by means of UV absorbance, and therefore know the exact time when the kidney substitution treatment liquid concentration is equilibrated with the blood one, either because the UV monitor displays a plateau, or because we estimate when the steady state will be reached by means of the first values of the exponential curve. Our approach delivers a more accurate value and eventually improves the equilibration time because of the recirculation.

In one embodiment of the invention the effluent kidney substitution treatment liquid is recirculated against the blood flowing through the kidney substitution after a predetermined treatment time or after the RR or the Kt/V, respectively, has reached a predetermined value. Thus it is possible to start the kidney substitution treatment at the time the concentration of the waste product in the blood is known, so that no error occurs while determining the Kt/V-Values or the reduction rate of the waste product.

In another advantage embodiment of the present invention the absorbance or the transmission of electromagnetic radiation is measured to determine the spectrophotometrical values of the effluent kidney substitution treatment liquid. The absorbance or the transmission of electromagnetic radiation are easily determinable especially if light, i.e, ultraviolet light is used as electromagnetic radiation.

Furthermore it is advantageously if the wavelength of the ultraviolet light is in the rang 180 nm to 380 nm. Even more advantageously it is if the wavelength of the ultraviolet light is in the rang 200 nm to 320 nm. The most intensive absorbance lines of almost every waste product in the blood are located in that ranges. For the determining of a special waste product, i.e at least one of urea, uric acid, creatinine, phosphates, B2 microglobuline, B12 vitamin or any other compound which has to be cleared from the blood of the patient, it is possible to select the most intensive absorbance line of that product. So the concentration of every waste product can be monitored on line in real time.

Furthermore every possible kidney substitution treatment, i.e hemodialysis, hemofiltration, pre-dilution hemofiltration, post-dilution hemofiltration, hemodiafiltration, pre-dilution hemodiafiltration or post-dilution hemodiafiltration is used with the present invention.

Another very advantageously feature of the present invention is that the determination of $A_{B(t)}$ is performed continuously. Thus the Kt/V-value or the reduction rate can be monitored continuously without any error, so that the adequacy and the effectiveness can be controlled at high quality.

DESCRIPTION OF PREFERRED EMBODIMENTS

The invention is now described with the help of a mathematical derivation.

Figure 1:
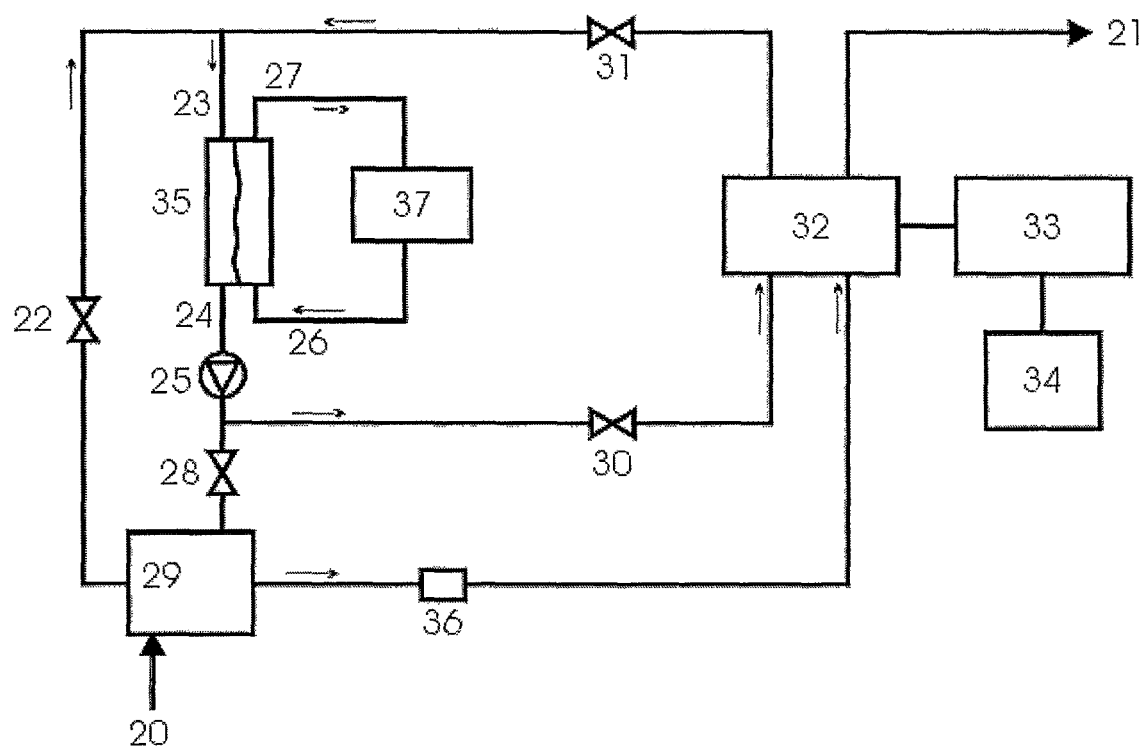
FIG. 1.: Depicts a portion of a modified kidney substitution treatment liquid circuit to allow recirculation of the kidney substitution treatment with the kidney substitution and a coupling with an UV spectrophotometer.

FIG. 1 shows a section of the kidney substitution treatment liquid circuit of a conventional kidney substitution treatment machine plus some modifications to host the kidney substitution treatment liquid recirculation functionality explained above. The conduit 20 carries the kidney substitution treatment liquid from a kidney substitution treatment liquid source (not shown). At the beginning of the treatment, after the kidney substitution treatment liquid composition has achieved the set requirements and all the tubes are rinsed, valves 22 and 28 are closed while valves 30 and 31 are open, pump 25 recirculates the rinsed kidney substitution treatment liquid with the kidney substitution, and the UV measuring system registers the offset (see below), then the patient is connected and the kidney substitution treatment liquid keeps on recirculating with the patient blood until equilibration is achieved. It is detected by an algorithm in the computer 33, then a feed back signal is sent and valves 22 and 28 are open while valves 30 and 31 are closed, setting the system in normal treatment mode. The flow sensor 36 gives an accurate kidney substitution treatment liquid flow measurement necessary for obtaining the "quantity of UV absorbance" value in each analyzed time interval. All the calculations described below are carried out by the computer 33.

Assuming that urea is distributed in a single pool volume in the body, that urea generation rate and ultrafiltration are negligible during the session Kt/V can be calculated as:

$$Kt/V = -\ln\frac{C_{Bt}}{C_{Bo}} \tag{1}$$

In equation 1 $C_{Bt}$ is the blood urea concentration at the end of the treatment, and $C_{Bo}$ is the blood urea concentration at the beginning of the treatment. According to equation 1 in order to calculate a Kt/V value the values of $C_{Bt}$ and $C_{Bo}$ are needed. The present invention allows to obtain such values in an indirect way.

On the kidney substitution treatment liquid side an UV absorbance A measurement is located which is linearly correlated with the urea concentration C in the blood of an individual patient. Therefore $A_D$ and $C_D$ functions over the time can be described as follows:

$$A_D(t) = A_{D0} \cdot e^{\frac{-Kt}{V}} \tag{2}$$

$$C_D(t) = A_D(t) \cdot a + b$$

In equation 2 $A_D$ is the UV absorbance in the kidney substitution treatment liquid, K is the clearance, t: treatment time, V is distribution volume of the waste product, $C_D$ is the concentration in the kidney substitution treatment liquid, a is a linear factor and b the offset.

Figure 2:
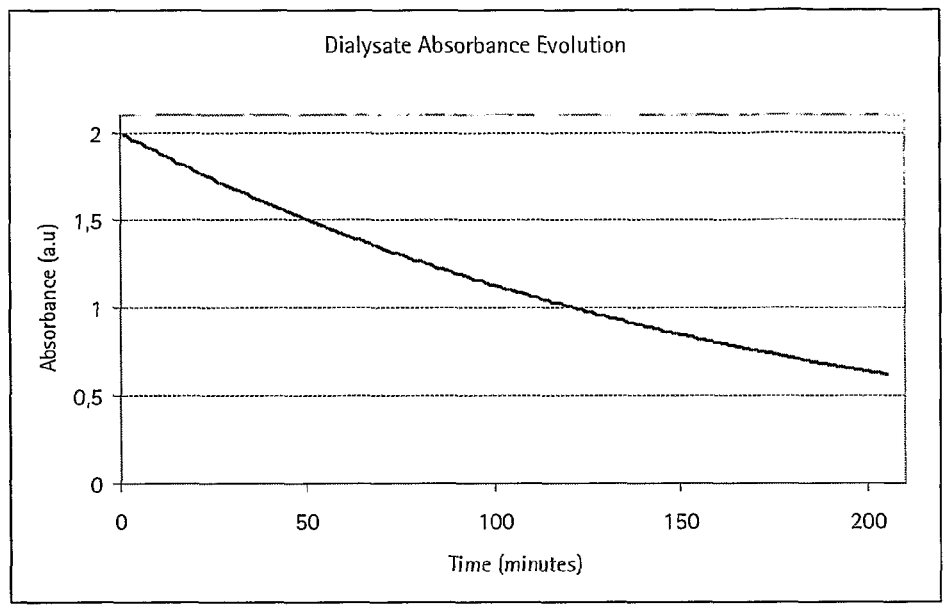
FIG. 2.: Graph with the theoretical evolution of the UV absorbance over the time in the kidney substitution treatment liquid side.

FIG. 2 shows a graph of the theoretical absorbance evolution over the time in the kidney substitution treatment liquid side.

In the $C_D(t)$ function the linear factor "a" is unknown but factor "b" represents the offset or the absorbance due to kidney substitution treatment liquid without waste product compounds. Therefore the factor "b" can be measured before starting the treatment, as shown in the description of FIG. 1 above and can be considered in any absorbance reading. Thus $C_D(t)$ function can be written as:

$$C_D(t) = A_D(t) \cdot a \tag{3}$$

Figure 3:
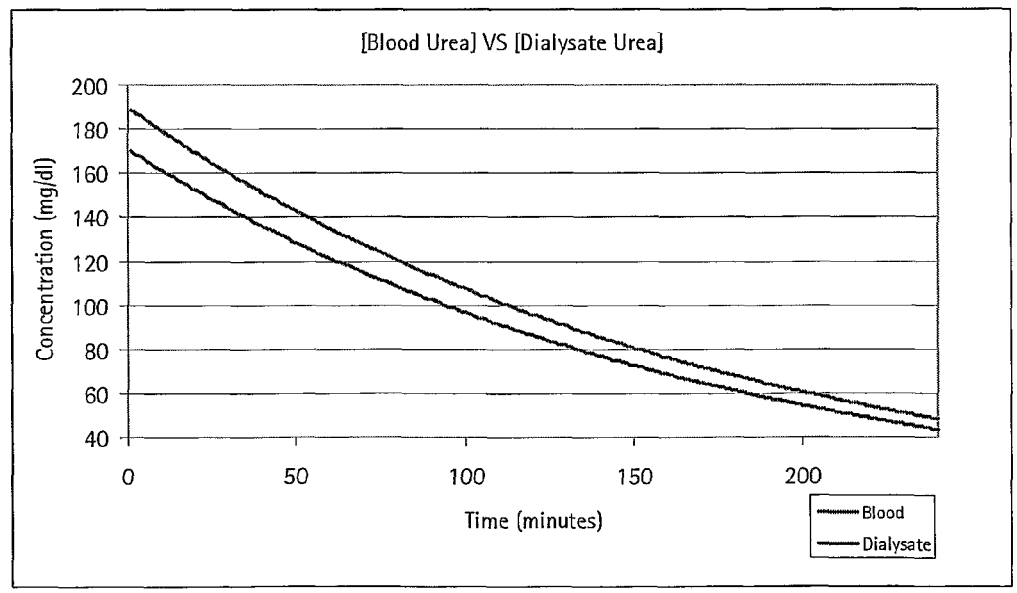
FIG. 3.: Graph with the theoretical relationship between kidney substitution treatment liquid urea concentration and blood urea concentration.
Figure 4:
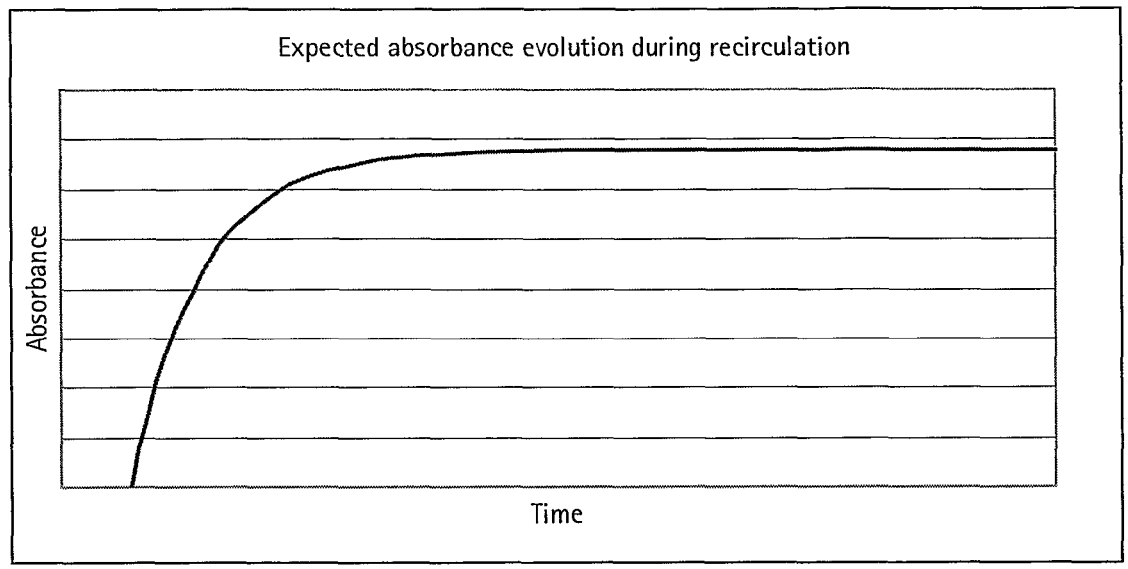
FIG. 4.: Graph with the theoretical evolution of the UV absorbance over the time in the kidney substitution treatment liquid side during the recirculation stage.
Figure 5:
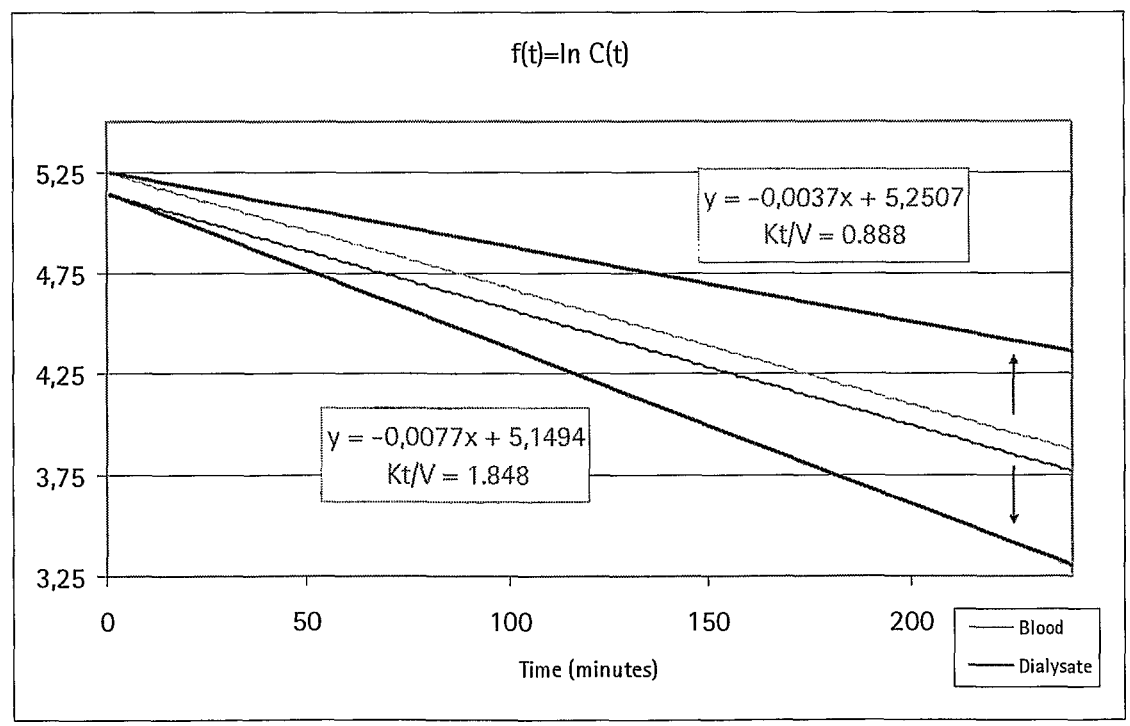
FIG. 5.: Graph depicting the Kt/V overestimation risk, when it is calculated by means of the slope of the line, which results after applying the natural logarithm to the evolution of the urea concentration in the kidney substitution treatment liquid side over the time.

During the treatment not all of the relevant waste product from the blood side moves into the kidney substitution treatment liquid side. If we assume the arbitrary hypothesis that 90% of the relevant blood waste product goes to the kidney substitution treatment liquid side and we plot some hypothetic concentrations over the time, we would get something like FIG. 3. In order to obtain $A_{Bo}$, which is the UV absorbance that would correspond to the initial blood waste product concentration, we need a waste product concentration in the kidney substitution treatment liquid equilibrated with the blood waste product concentration. Thus we need to recirculate the kidney substitution treatment liquid with the blood as described above. If we plot the UV absorbance over the time during the recirculation stage we get something like FIG. 4.

UV absorbance monitoring over the time allows us to determine and record $A_{Bo}$ either waiting until the absorbance A arrives to a steady state, or estimating when such steady state is reached by means of the first values of the exponential function.

With an estimation of the waste product distribution volume it is possible to calculate the quantity of the waste product $U_{B0}$ within the body before starting the treatment:

$$U_{Bo} = C_{Bo} \cdot V \quad (4)$$

If we multiply $A_{Bo}$ and V, we can get a new parameter analog to the waste product mass, and we can name it "quantity of UV absorbance" and represent it as D, therefore we can write:

$$D_{Bo} = A_{Bo} \cdot V \quad (5)$$

If we know $A_{Bo}$, and V by means of bioimpedance, UKM or anthropometric estimation we can obtain $D_{Bo}$, which is the key value to later calculate Kt/V.

If we compute the area under $f(A_D)$ multiplied by the kidney substitution treatment liquid flow, we get the quantity of UV absorbance $D_D$ extracted from the patient in each desired interval of time, therefore:

$$Q_D \cdot \int_0^t f(A_D) dt = \Delta D_D \quad (6)$$

Applying simple mass balance we can obtain the "quantity of absorbance" $D_{Bt}$ remaining on the patient:

$$D_{Bo} + \Delta D_D = D_{Bt} \quad (7)$$

Applying the same principle used in equation 4, we can compute $A_{Bt}$, which is the UV absorbance that we would get if we were able to directly measure the blood waste product absorbance at the time t:

$$D_{Bt} = A_{Bt} \cdot (V - UF_t) \quad (8)$$

Combining equations 1 and 2 it is possible to write:

$$Kt/V = -\ln\frac{C_{Bt}}{C_{Bo}} = -\ln\frac{f(A_{Bt})}{f(A_{Bo})} = -\ln\frac{A_{Bt} \cdot a}{A_{Bo} \cdot a} = -\ln\frac{A_{Bt}}{A_{Bo}} \quad (9)$$

The final step would be apply Daugirda's single pool formula to account for waste product generation during the treatment, but not for volume contraction as it is already considered in equation 8.

Applying this method it is also possible to online calculate the Reduction Ratio (RR) of the waste product:

$$RR = 1 - \frac{C_{Bt}}{C_{Bo}} = 1 - \frac{A_{Bt} \cdot a}{A_{Bo} \cdot a} = 1 - \frac{A_{Bt}}{A_{Bo}} \quad (10)$$

Since during the equilibration stage at the beginning of the treatment, the waste product inbound effect has not been yet established, and considering that the final waste product concentration is not measured but estimated by means of the extracted "quantity of UV absorbance", the obtained Kt/V value considers waste product rebound, and therefore should be an equilibrated Kt/V value.

It is also possible recirculate the kidney substitution treatment liquid with the blood at the end of the treatment, and calculate by these means a single pool Kt/V. In that way it is possible to determine the final waste product concentration by recirculating the kidney substitution treatment liquid at the end of the kidney substitution treatment in the same way as at the beginning of the kidney substitution treatment. Therefore the values 22 and 28 of the kidney substitution treatment liquid conduit are closed while the values 30 an 31 of the kidney substitution treatment liquid conduit are opened. Then the kidney substitution treatment liquid is recirculating through the kidney substitution 35 as long as the absorbance A measured with the UV spectrophotometer 32 is not constant. If the absorbance A reaches a constant value the concentration of the waste product in the recirculated kidney substitution treatment liquid is the same as in the blood of the patient. The concentration is now equilibrated.

Adjusting the spectrophotometer wavelength and applying the described method it is possible to estimate Kt/V and reduction ratios for many important compounds like urea, $\beta 2$-microglobulin, uric acid, creatinine, phosphates or the like.

Figure 6:
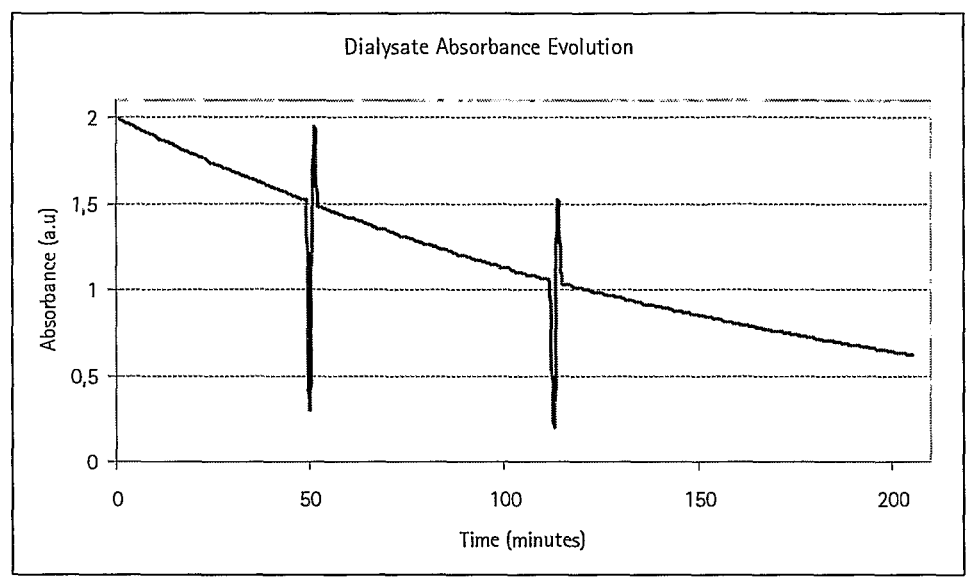
FIG. 6.: Graph depicting the absorbance spike caused by stationary kidney substitution treatment liquid within the kidney substitution during bypass mode.

Another possible embodiment is to apply the method described in the already mentioned patent WO 94/08641, but using the UV approach instead of an urea sensor, since UV reliability and stability is better. Fridolin et al have observed absorbance spikes due to stationary kidney substitution treatment liquid in the kidney substitution when working with real kidney substitution treatments. During a normal treatment, when the machine turns into bypass mode due to some alarm, the kidney substitution treatment liquid flow through the kidney substitution is stopped, as a result a sudden decrease in the UV absorbance is noticed. Nevertheless compounds diffusion from blood to kidney substitution treatment liquid carries on increasing the concentration on the kidney substitution treatment liquid until it reaches the equilibration level. When the treatment mode is restarted, the compounds concentration in the kidney substitution treatment liquid volume within the kidney substitution is higher, and therefore a transitory increased UV absorbance is noticed as a positive spike over the baseline level existing before starting the bypass mode. FIG. 6. This stationary flow based spike could be used to determine pre-dialysis waste product blood concentration and if required, post-dialysis blood waste product concentration. In such approach the recirculation design proposed in FIG. 1 wouldn't be necessary.

Since the proposed invention is based on total solute extraction from the patient and not in creating a diffusive gradient between blood and kidney substitution treatment liquid like the conductivity based methods, it is applicable not only to diffusion based treatments but also to convection based treatments, therefore it can monitor the adequacy of any of the available kidney substitution treatments.

LIST OF REFERENCE SIGNS

20—kidney substitution liquid source
21—kidney substitution liquid drain
22—valve
23—kidney substitution liquid inlet
24—kidney substitution liquid outlet
25—pump
26—blood inlet 27—blood outlet
28—valve
29—balance chamber
30—valve
31—valve
32—measuring device, spectrophotometer, UV spectrophotometer
33—computer
34—display
35—kidney substitution device
36—flow sensor
37—patient

The invention claimed is:

1. An apparatus for determining a reduction ratio (RR) or a Kt/V value of a kidney substitution treatment comprising:
a kidney substitution device;
an external blood circuit which is connected to the kidney substitution device;
a kidney substitution liquid conduit system which is connected to the kidney substitution device, a kidney substitution liquid source and a kidney substitution liquid drain wherein the kidney substitution liquid conduit system comprises a valve system to recirculate the effluent kidney substitution treatment liquid of the kidney substitution device to the kidney substitution device;
a measuring device for determining spectrophotometric values of the effluent kidney substitution treatment liquid located at the outflow of the kidney substitution treatment liquid conduit between the kidney substitution device and the kidney substitution liquid drain such that the effluent kidney substitution liquid either has to pass the measuring device during recirculation or has to pass the measuring device as it flows into the kidney substitution liquid drain; and
a computer,
wherein the valve system comprises a first valve between the kidney substitution liquid source and the kidney substitution device, a second valve between the kidney substitution liquid drain and the kidney substitution device, and a third and fourth valve in a kidney substitution liquid circuit,
wherein a pump recirculates the effluent kidney substitution treatment liquid against the blood flowing through the kidney substitution while the first valve and the second valve are closed and while the third and fourth valve are opened until the computer detects that the spectrophotometrical value of the effluent kidney substitution treatment liquid has reached a constant value $A_{B0}$, and wherein the reduction ratio (RR) of the at least one waste product is determined by the computer with the equation $$RR = 1 \frac{A_{B(t)}}{A_{B_0}}$$

or the Kt/V value is determined by the computer with the equation $$Kt/V = -1n \frac{A_{B(t)}}{A_{B_0}}$$

wherein $A_{B(t)}$ is the spectrophotometrical value on the effluent kidney substitution treatment liquid at the treatment time t during the kidney substitution treatment which is commenced after the recirculation of the effluent kidney substitution treatment liquid and wherein K is the effective clearance of the waste product and V is the distribution volume of the waste product.

2. Apparatus according to claim 1, characterized in that the measuring device is a spectrophotometer.

3. Apparatus according to claim 1, characterized in that the measuring device is an UV spectrophotometer.

4. The apparatus of claim 2, wherein the spectrophotometer measures the absorbance or transmission of electromagnetic radiation to determine the spectrophotometrical values of the effluent kidney substitution treatment liquid.

5. The apparatus of claim 4, wherein ultraviolet light is used as the electromagnetic radiation.

6. The apparatus of claim 5, wherein the wavelength of the ultraviolet light is in the range 180 nm to 380 nm.

7. The apparatus of claim 6, wherein the wavelength of the ultraviolet light is in the range 200 nm to 320 nm.

* * * * *

UNITED STATES PATENT AND TRADEMARK OFFICE
CERTIFICATE OF CORRECTION

PATENT NO. : 8,702,979 B2  Page 1 of 1
APPLICATION NO. : 12/665150
DATED : April 22, 2014
INVENTOR(S) : Alex Castellarnau It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1056 days.

Signed and Sealed this

Twenty-ninth Day of September, 2015

Michelle K. Lee
*Director of the United States Patent and Trademark Office*